(12) United States Patent
Hsu

(10) Patent No.: US 8,840,776 B2
(45) Date of Patent: Sep. 23, 2014

(54) METHOD AND SENSOR STRIP FOR ANALYSIS OF A SAMPLE

(75) Inventor: Cheng-Teng Hsu, Taichung (TW)

(73) Assignee: Bionime Corporation, Taichung (TW)

( * ) Notice: Subject to any disclaimer, the term of this patent is extended or adjusted under 35 U.S.C. 154(b) by 0 days.

(21) Appl. No.: 13/617,826

(22) Filed: Sep. 14, 2012

(65) Prior Publication Data

US 2013/0098776 A1 Apr. 25, 2013

(30) Foreign Application Priority Data

Oct. 25, 2011 (TW) .............................. 100138686 A

(51) Int. Cl.
*G01N 27/327* (2006.01)
*C12Q 1/00* (2006.01)

(52) U.S. Cl.
CPC ............ *G01N 27/3272* (2013.01); *C12Q 1/006* (2013.01)
USPC .... 205/792; 205/777.5; 422/68.1; 422/82.01; 435/287.1; 204/403.01

(58) Field of Classification Search
USPC .............................. 205/775, 777.5, 778, 792; 204/403.01–403.15; 600/345–348; 422/68.1; 435/287.1, 287.2
See application file for complete search history.

(56) References Cited

U.S. PATENT DOCUMENTS

| | | | | |
|---|---|---|---|---|
| 2007/0246357 A1* | 10/2007 | Wu | .......................... | 204/403.01 |
| 2008/0217171 A1* | 9/2008 | Jang | ......................... | 204/403.14 |
| 2010/0206749 A1* | 8/2010 | Choi | ........................... | 205/777.5 |
| 2011/0297557 A1* | 12/2011 | Wu et al. | ....................... | 205/792 |
| 2012/0080326 A1* | 4/2012 | Chatelier et al. | .............. | 205/782 |

* cited by examiner

*Primary Examiner* — Jennifer Dieterle
(74) *Attorney, Agent, or Firm* — Steptoe & Johnson LLP

(57) ABSTRACT

A method for estimation of hematocrit of a sample having an analyte includes: bringing the sample into contact with a sensor strip including a reference electrode coated with a reference layer nonreactive to the analyte, and a working electrode coated with a working layer including a biorecognition element reactive to the analyte; applying a voltage between the reference and working electrodes, and recording information of a reaction current flowing through the sample within a time period of not greater than 5 seconds from beginning of application of the voltage; and estimating the hematocrit of the sample by analyzing the recorded information using a predetermined current-hematocrit function.

16 Claims, 16 Drawing Sheets

First Database

| Hct(%) | 100mg/dL | 200mg/dL | 300mg/dL | all mean |
|---|---|---|---|---|
| 25 | 78.83847 | 82.43293 | 80.4175333 | 80.56298 |
| 42 | 85.72107 | 87.9349 | 88.6362 | 87.43072 |
| 55 | 95.06493 | 97.5891 | 97.9932 | 96.88241 |
| 70 | 108.1572 | 104.9427 | 106.2944 | 106.4648 |

Second Database

| Hct(%) | Mean of 100mg/dL | Mean of 200mg/dL | Mean of 300mg/dL |
|---|---|---|---|
| 25 | 383.71 | 694.07 | 1061.00 |
| 42 | 393.91 | 643.07 | 988.33 |
| 55 | 381.04 | 646.52 | 873.71 |
| 70 | 379.34 | 576.14 | 696.09 |

FIG. 12(A)

Correction Factor Database

| Hct(%) | Mean of 100mg/dL | Mean of 200mg/dL | Mean of 300mg/dL |
|---|---|---|---|
| 25 | 1.03 | 0.93 | 0.93 |
| 42 | 1 | 1 | 1 |
| 55 | 1.03 | 0.99 | 1.13 |
| 70 | 1.04 | 1.12 | 1.42 |

FIG. 12(B)

METHOD AND SENSOR STRIP FOR ANALYSIS OF A SAMPLE

CROSS-REFERENCE TO RELATED APPLICATION

This application claims priority to Taiwanese Application No. 100138686, filed on Oct. 25, 2011.

BACKGROUND OF THE INVENTION

1. Field of the Invention

The invention relates to an electrochemical measuring method, and more particularly to an electrochemical measuring method and a sensor strip used therein.

2. Description of the Related Art

Generally, measurement of an analyte using an electrochemical method has some limitations. In a reaction zone with finite volume, composition of the sample to be analyzed may have influence on precision of the measurement result. For example, in the measurement of the concentration of the analyte in blood, composition of the blood contributes a lot of influences. In particular, hematocrit, which represents a ratio of the red blood cells in the blood, is a major factor contributing to an incorrect measurement result. Normal hematocrit of a person usually ranges from 35% to 45%. However, hematocrit of some people may range between 20% and 60%.

In an electrochemical bio-sensing process, different hematocrits may result in different effects. Taking a blood glucose measurement for example, a low hematocrit may lead to a high measurement result, and a high hematocrit may lead to a low measurement result. For the high hematocrit, the red blood cells may: (1) impede reaction between an enzyme and an electrochemical mediator; (2) result in lower chemical dissolution due to small amount of the blood plasma that dissolves the chemical reactant; and (3) slow down diffusion of the mediator. These factors may cause lower electric current produced during electrochemical reaction, thereby resulting in the measured glucose level being lower than the actual glucose level. The low hematocrit, on the other hand, leads to an opposite result. Moreover, impedance of the blood specimen is also influenced by the hematocrit, and thus having effect on measurement of voltage and/or current.

Several methods have been proposed to alleviate adverse influence of hematocrit. For example, U.S. Pat. No. 5,628,890 discloses a sensor strip including a mesh layer to remove the red blood cells from the sample. However, this method results in higher cost, complexity of the sensor strip, and higher requirement of test time and sample volume.

Another method employs an electrochemical method to measure electrochemical signals, such as construction of a hematocrit correction function of the sample by use of the measured resistance or current, so as to correct concentration of the analyte in the sample. One such electrochemical measuring method is disclosed in U.S. Pat. No. 6,890,421. In this method, the sensor strip includes two metalized electrodes disposed in a sandwich configuration. The sensor strip has a reaction zone filled with a reagent including a mediator for enhancement of electron transfer and an enzyme. After introducing the blood to be analyzed into the reaction zone, a first voltage is applied to the reaction zone filled with the blood for 3 to 20 seconds, followed by applying a second voltage, which has an opposite polarity to the first voltage, to the reaction zone filled with the blood for 1 to 10 seconds. Then, the detected first and/or second sensing current resulting from application of the first and second voltages is used to calculate an initial concentration of the analyte in the blood and a hematocrit correction factor. The hematocrit correction factor is a specific value or a function used for correcting the measured value of the initial concentration. As an example, the estimated concentration of the analyte in the sample may be obtained by subtracting a background value from the measured value of the initial concentration, followed by multiplication with the hematocrit correction faction.

In this method, since the two electrodes are influenced by the hematocrit and the concentration of the analyte during both applications of the first and second voltages, the generated first and second sensing currents are also influenced, thereby resulting in deviation of the estimated hematocrit. Then, the estimated concentration of the analyte also deviates and may lead to a wrong conclusion based on a report using these data. On the other hand, data processing used in this technique is complicated because determination of the hematocrit correction factor and calculation of the initial concentration of the analyte must be done prior to obtaining the corrected concentration value. Therefore, there is a need to develop a relatively simple method and a system that can remove interference of the hematocrit so as to achieve high precision of the measurement result.

SUMMARY OF THE INVENTION

Therefore, an object of the present invention is to provide a method for estimation of hematocrit and concentration of an analyte in a sample with high precision.

According to one aspect of the present invention, a method for estimation of hematocrit of a sample having an analyte, comprises:

a) bringing the sample into contact with a sensor strip, the sensor strip including a reference electrode coated with a reference layer, and a working electrode coated with a working layer, the reference layer being nonreactive to the analyte, the working layer including a mediator for enhancement of electron transfer, and a biorecognition element reactive to the analyte;

b) applying a voltage between the reference electrode and the working electrode, such that an electrical potential at the reference electrode is higher than that at the working electrode, and recording information of a reaction current flowing through the sample as a result of application of the voltage within a time period of not greater than 5 seconds from beginning of application of the voltage, wherein the information is related to the hematocrit of the sample and is unrelated to the analyte in the sample; and c) estimating the hematocrit of the sample by analyzing the recorded information using a predetermined current-hematocrit function.

According to another aspect of the present invention, a method for estimation of concentration of an analyte in a sample, comprises:

a) bringing the sample into contact with a sensor strip, the sensor strip including a reference electrode coated with a reference layer, and a working electrode coated with a working layer, the reference layer being nonreactive to the analyte, the working layer including a mediator for enhancement of electron transfer, and a biorecognition element reactive to the analyte;

b) applying a first voltage between the reference electrode and the working electrode, such that an electrical potential at the reference electrode is higher than that at the working electrode, and recording first information of a reaction current flowing through the sample as a result of application of the first voltage, wherein the first information is related to hematocrit of the sample and is unrelated to the analyte in the sample;

c) estimating the hematocrit of the sample by analyzing the recorded first information using a predetermined current-hematocrit function;

d) applying a second voltage between the reference electrode and the working electrode, such that an electrical potential at the reference electrode is lower than that at the working electrode, and recording second information of a reaction current flowing through the sample as a result of application of the second voltage, wherein the second information is related to the concentration of the analyte in the sample; and e) estimating the concentration of the analyte in the sample based on the hematocrit of the sample estimated in step c) and the second information recorded in step d).

Another object of the present invention is to provide a sensor strip for use with a measuring apparatus to estimate concentration of an analyte in a sample.

According to another aspect of the present invention, a sensor strip comprises:

a strip body formed with a groove for receiving the sample;

a reference electrode adjacent to the groove and to be electrical contacted to the measuring apparatus;

a working electrode spaced apart from the reference electrode, adjacent to the groove, and to be electrical contacted to the measuring apparatus;

a reference layer coated on the reference electrode, and including a mediator for enhancing electron transfer, and a hydrophilic chemical substance; and a working layer coated on the working electrode, and including a mediator for enhancing electron transfer, a biorecognition element reactive to the analyte, and a hydrophilic chemical substance.

BRIEF DESCRIPTION OF THE DRAWINGS

Other features and advantages of the present invention will become apparent in the following detailed description of the preferred embodiment with reference to the accompanying drawings, of which:

FIGS. 12(A) to 12(C) are a table showing a second database, a table showing a correction factor database, and a plot according to the second database of the example of the present invention.

DETAILED DESCRIPTION OF THE PREFERRED EMBODIMENT

Figure 1:
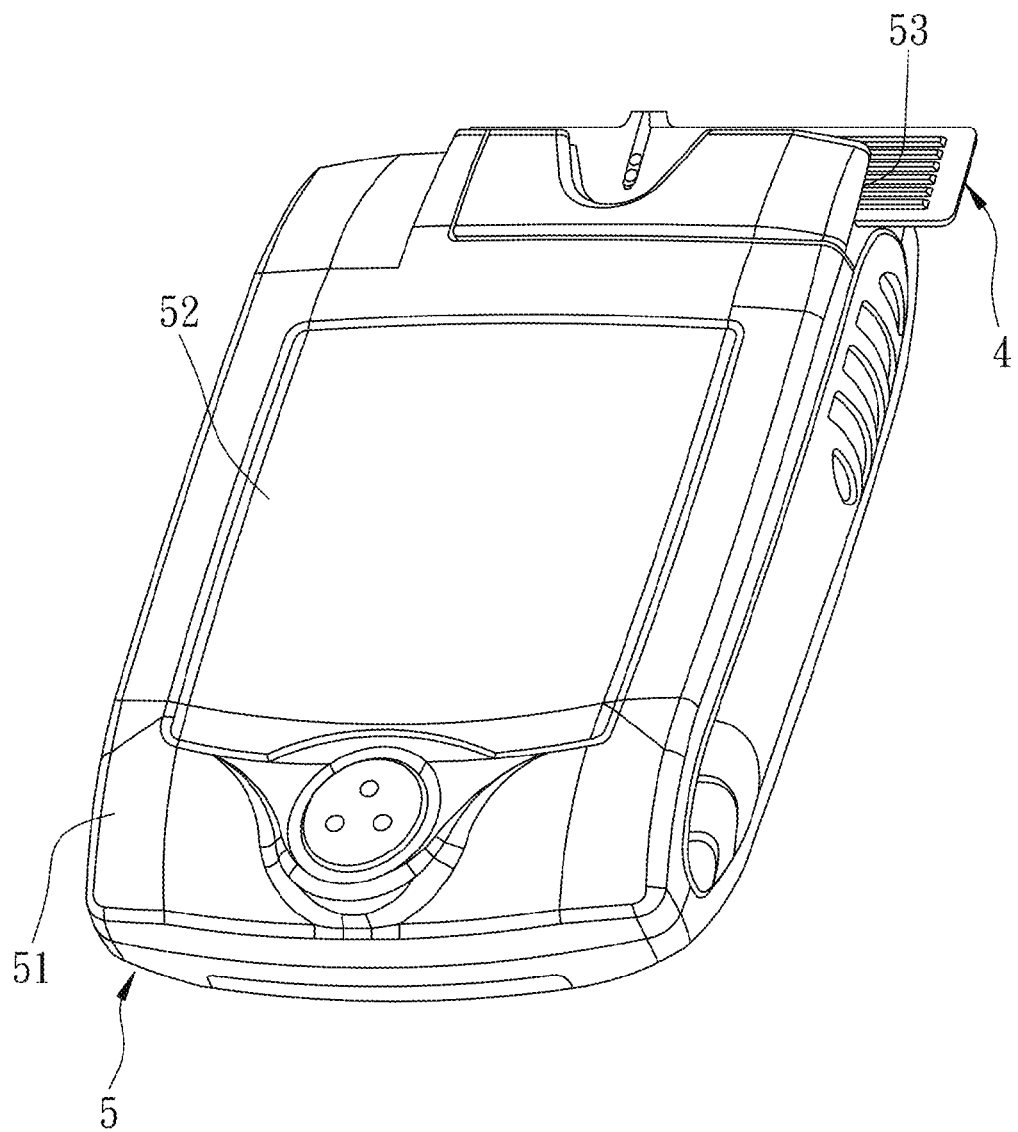
FIG. 1 is a perspective view showing a preferred embodiment of the sensor strip and the measuring device according to the present invention.
Figure 2:
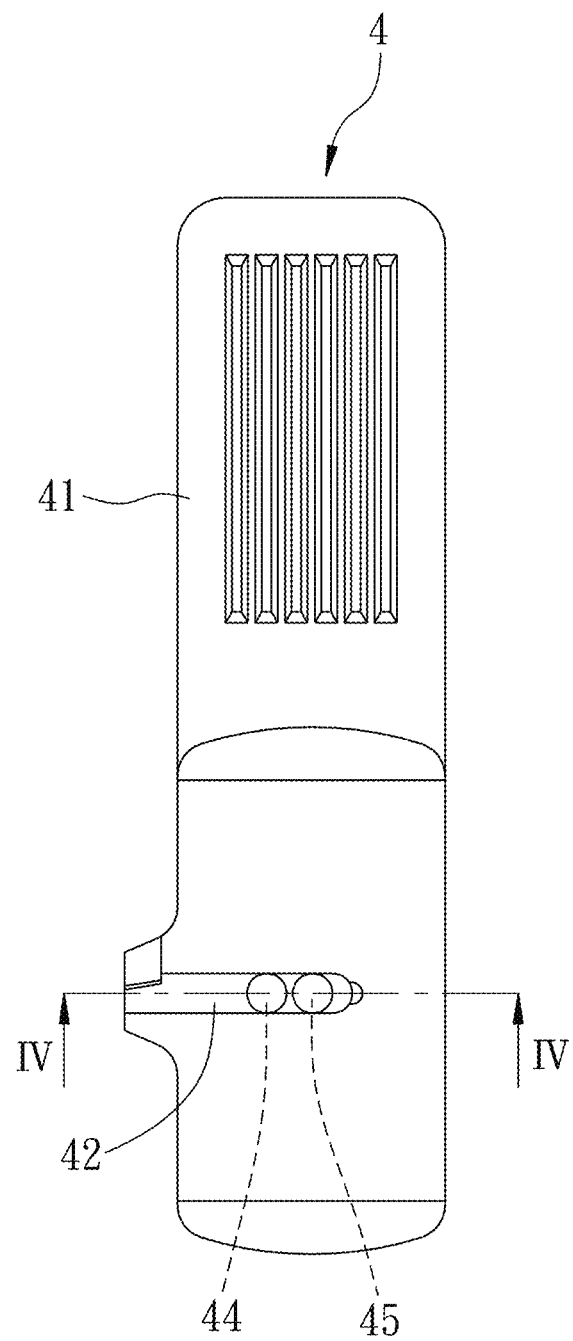
FIG. 2 is a top view of the sensor strip of the preferred embodiment.

Referring to FIG. 1 and FIG. 2, the preferred embodiment of the method according to this invention is applied to a sample including an analyte for estimation of hematocrit (HCT) of the sample, and concentration of the analyte in the sample. The method is implemented using a sensor strip 4 and a measuring device 5 for receiving the sensor strip 4. In this embodiment, the sample may be blood, and a biorecognition element may be an enzyme reactive to the analyte, or an antibody, a nucleic acid, a receptor, a chemical substance, etc., which is reactive to the analyte. The sensor strip 4 is an electrochemical sensor strip.

Figure 3:
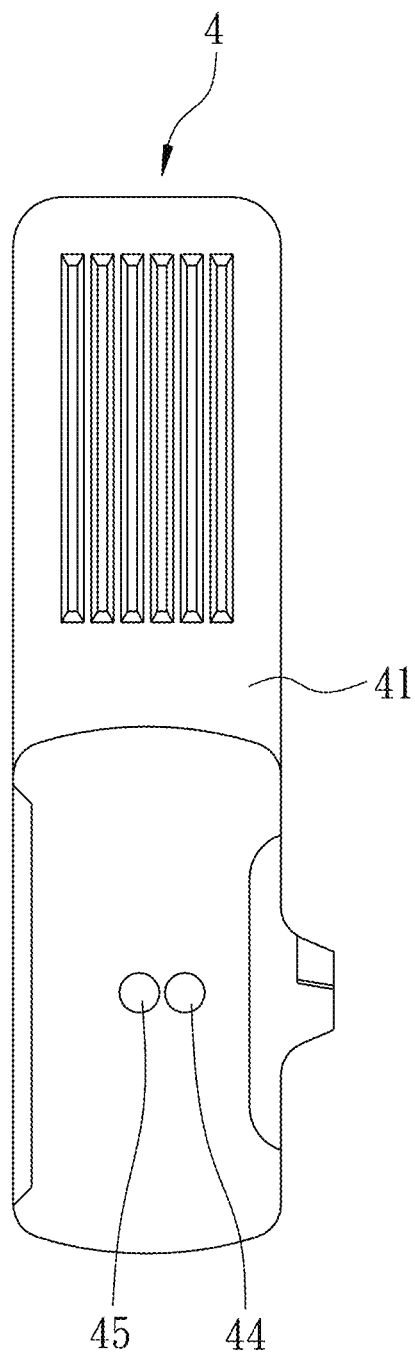
FIG. 3 is a bottom view of the sensor strip of the preferred embodiment.
Figure 4:
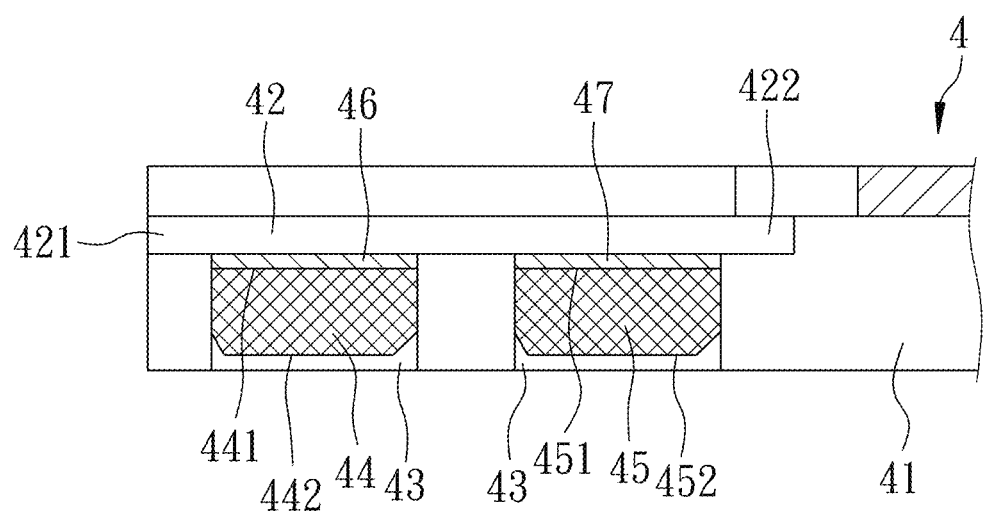
FIG. 4 is a sectional view showing the sensor strip taken along line IV-IV in FIG. 2.

Referring to FIGS. 2, 3, and 4, the sensor strip 4 comprises a strip body 41 formed with a groove 42 for receiving the sample, two through holes 43 in spatial communication with the groove 42, reference and working electrodes 44, 45 respectively disposed in the through holes 43, and reference and working layers 46, 47 coated on the reference and working electrodes 44, 45, respectively.

In this embodiment, the reference and working electrodes 44, 45 are disposed side by side on a same plane, but arrangements thereof are not limited thereto, ex, face to face arrangement is also included. The groove 42 has a sample inlet 421 for introducing the sample and located closer to the reference electrode 44 than the working electrode 45, but may be otherwise in other embodiments.

The groove 42 further has a sample outlet 422 opposite to the sample inlet 421. The reference electrode 44 has a circular reference surface 441 coated with the reference layer 46, and a first output surface 442 opposite to the reference surface 441. The working electrode 45 has a circular working surface 451 coated with the working layer 47, and a second output surface 452 opposite to the working surface 451.

The reference layer 46 includes a mediator for enhancement of electron transfer, and a hydrophilic chemical substance, but does not include any biorecognition element reactive to the analyte.

The working layer 47 includes a mediator for enhancement of electron transfer, a biorecognition element reactive to the analyte, and a hydrophilic chemical substance.

The mediator of the reference layer 46 and the working layer 47 may be any one of the following substances: a ferricyanide, a ferrocene or a derivative thereof, a ruthenium-containing substance, such as a ruthenium hexamine trichloride, a brilliant cresyl blue, an osmium bipyridyl complex, a derivative of quinone, and combinations thereof.

The biorecognition element may be an enzyme selected from: a glucose oxidase, a glucose dehydrogenase (GDH) with pyrroloquinoline quinine (PQQ), a GDH with nicotinamide adenine dinucleotide (NAD), and a GDH with flavin adenine dinucleotide (FAD).

The mediator of the reference layer 46 and that of the working layer 47 may be the same or different. When applied with an external voltage, the mediators may be oxidized or reduced. The hydrophilic chemical substance serves to enhance adhesion between substances on the reference and working layers 46, 47 (such as the biorecognition element) and the reference and working electrodes 44, 45. The hydrophilic chemical substance may be a surfactant (such as tween20, triton X-100, surfynol, mega 8), a soluble cellulose (such as methylcellulose (MC), carboxymethyl cellulose (CMC), methylhydroxyethylcellulose (MHEC), methylhydroxypropylcellulose (MHPC), hydroxyethylcellulose (HEC), hydroxyethylcarboxymethylcellulose (HECMC), carboxymethylhydroxyethylcellulose (CMHEC), and combinations thereof), a polyethylene glycol, a polyvinylpyrrolidone, a tackifier, a hydrophilic block copolymer, a polyacrylic acid, etc.

In addition to the mediator and the hydrophilic chemical substance, the reference layer 46 may further include substances that may aid in measurement of the hematocrit of the sample, such as an anionic surfactant for enhancing reaction between the heme and the mediator, non-limiting examples of which include sodium dodecyl sulfate, sodium dodecyl sulfonate, desoxycholic acid and derivatives thereof. Moreover, the reference layer 46 may further include a stabilizer, a buffer solution, and a surfactant.

Figure 5:
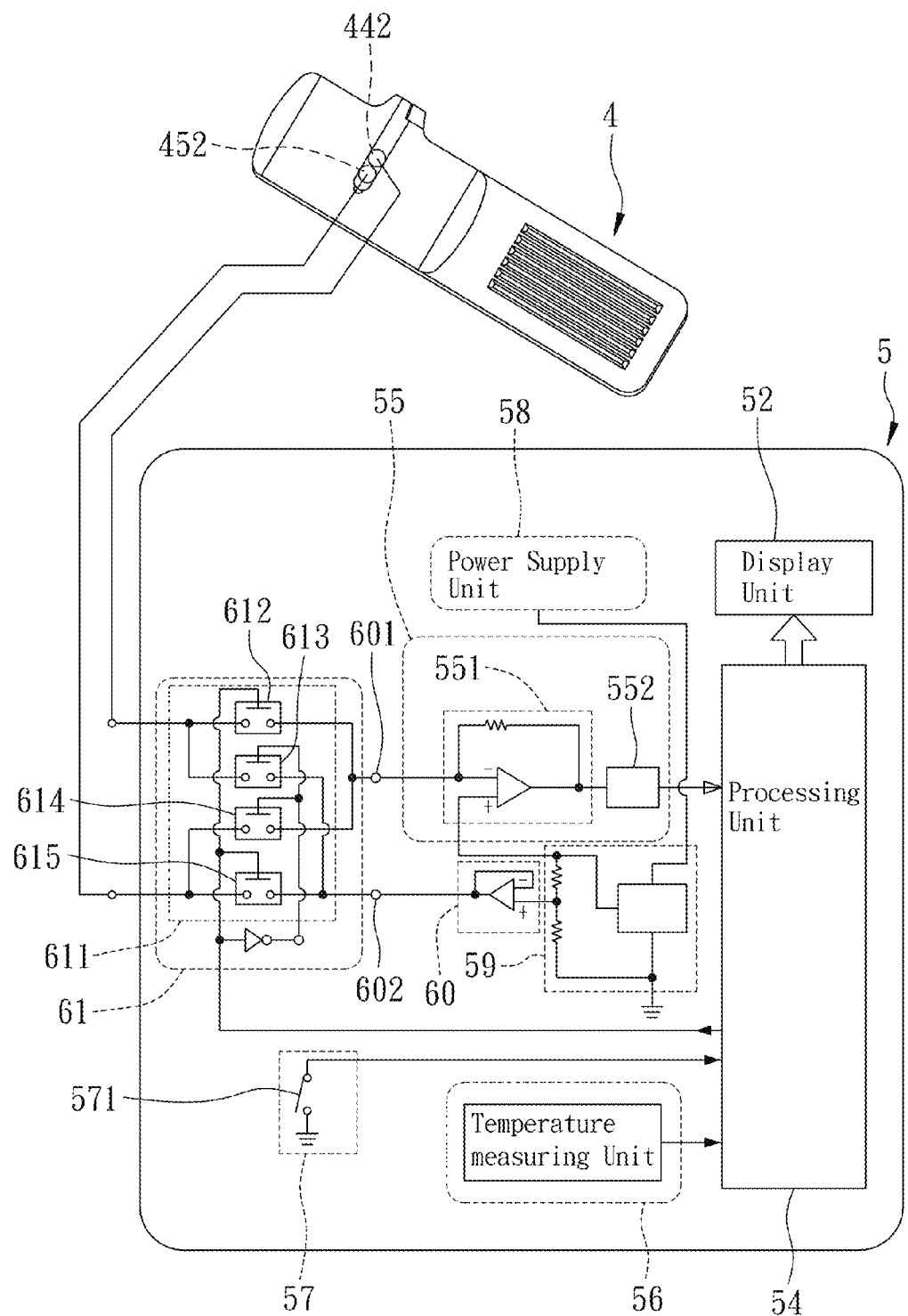
FIG. 5 is a circuit diagram of the measuring device.

In this embodiment, referring to FIGS. 1, 4, and 5, the measuring device 5 includes a housing 51, a display unit 52 connected to the housing 51 and operable to display a measurement result, a slot 53 for receiving the sensor strip 4, a processing unit 54 electrical contacted to the display unit 52, a current measuring unit 55 electrical contacted to the processing unit 54, a temperature measuring unit 56 electrical contacted to the processing unit 54, a detecting unit 57 to be electrical contacted to the sensor strip 4, electrical contacted to the processing unit 54, and having a switch 571, a power supply unit 58, a voltage adjusting unit 59 electrical contacted to the power supply unit 58, a current buffer unit 60 electrical contacted to the voltage adjusting unit 59, and a voltage switching unit 61.

The current measuring unit 55 includes a current-to-voltage converting module 551 and an analog-to-digital converting module 552. The current-to-voltage converting module 551 is operable to convert a current between nodes 601, 602 into an analog voltage, and the analog-to-digital converting module 552 is operable to convert the converted analog voltage into an equivalent digital signal for subsequent computation by the processing unit 54.

The voltage adjusting unit 59 is used for applying voltage to the current buffer unit 60 that is capable of driving large currents, so as to generate a working potential on the node 602.

The voltage switching unit 61 is electrical contacted to the processing unit 54, the current measuring unit 55, the current buffer unit 60, and the first and second output surfaces 442, 452 of the sensor strip 4, and includes a switch set 611 controlled by the processing unit 54.

The switch set 611 includes four switches 612, 613, 614 and 615, and is controlled by the processing unit 54 to switch between a first switch mode and a second switch mode. In this embodiment, the switches 612, 613, 614 and 615 are IC-type analog switches, but may also be relays or bridges composed of transistors, such as metal-oxide-semiconductor field-effect transistors (MOSFET) or bipolar transistors.

Figure 6:
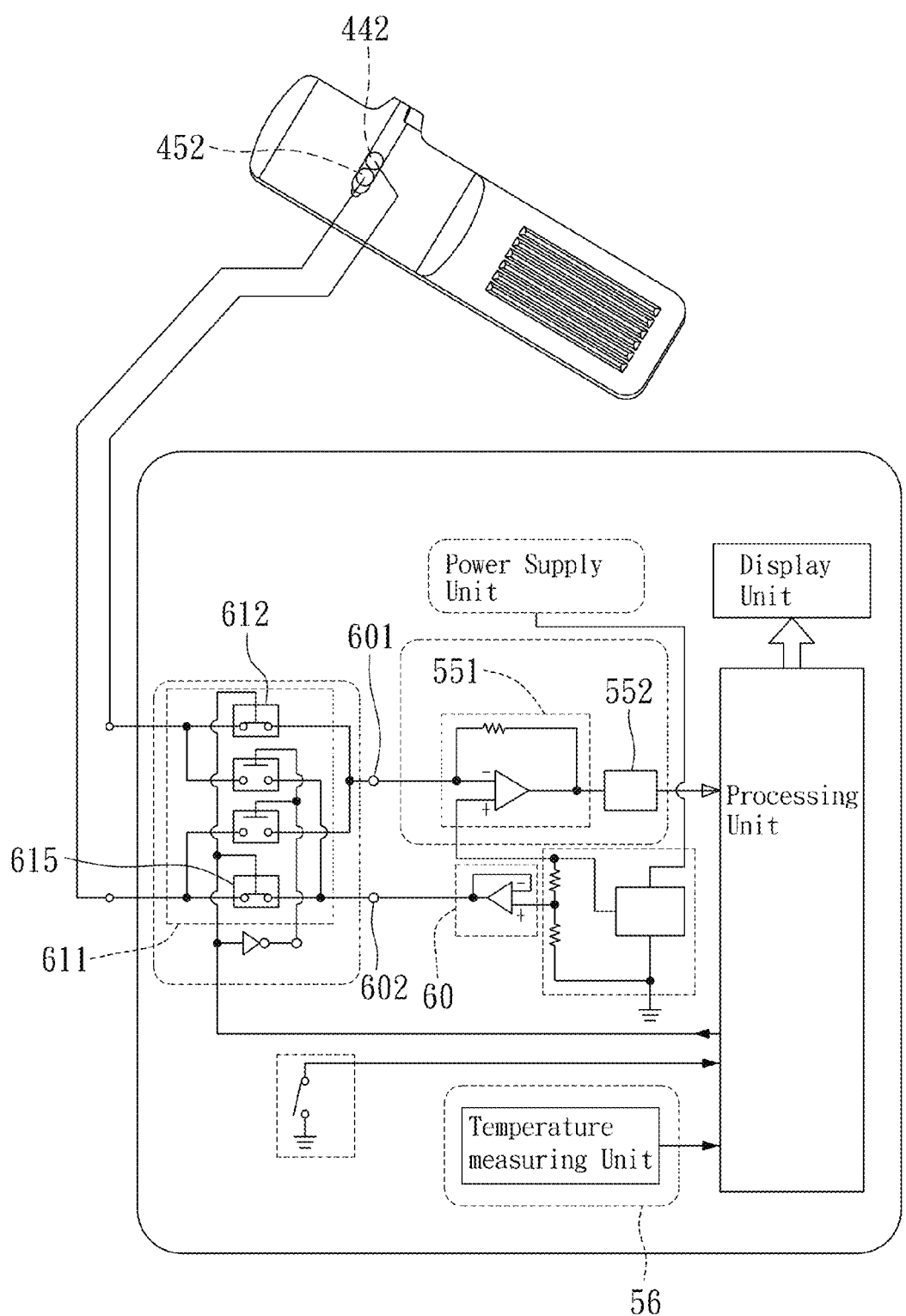
FIG. 6 is a circuit diagram showing the measuring device operated in a first switch mode.

Referring to FIG. 4 and FIG. 6, when the switch set 611 is operated in the first switch mode, the switches 612, 615 simultaneously conduct. At this time, the node 601 is conducted with the first output surface 442, and the node 602 is conducted with the second output surface 452. When the working potential generated by the current buffer unit 60 is lower than the potential at the node 601, the reference electrode 44 and the working electrode 45 receive a first voltage.

Figure 7:
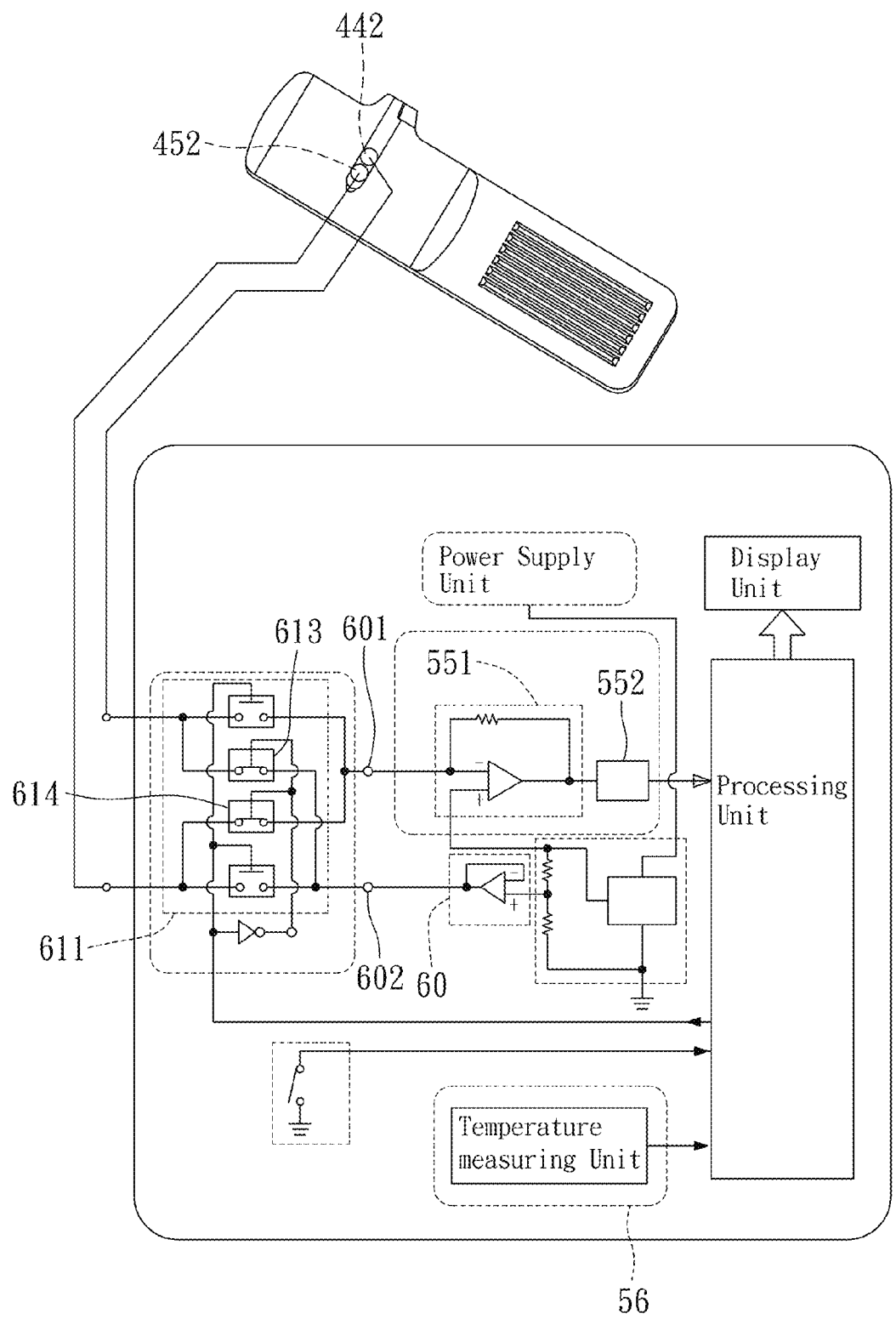
FIG. 7 is a circuit diagram showing the measuring device operated in a second switch mode.

Referring to FIG. 4 and FIG. 7, when the switch set 611 is operated in the second switch mode, the switches 613, 614 simultaneously conduct. At this time, the node 602 is conducted with the first output surface 442, and the node 601 is conducted with the second output surface 452. When the working potential generated by the current buffer unit 60 is lower than the potential at the node 601, the reference electrode 44 and the working electrode 45 receive a second voltage.

Figure 8:
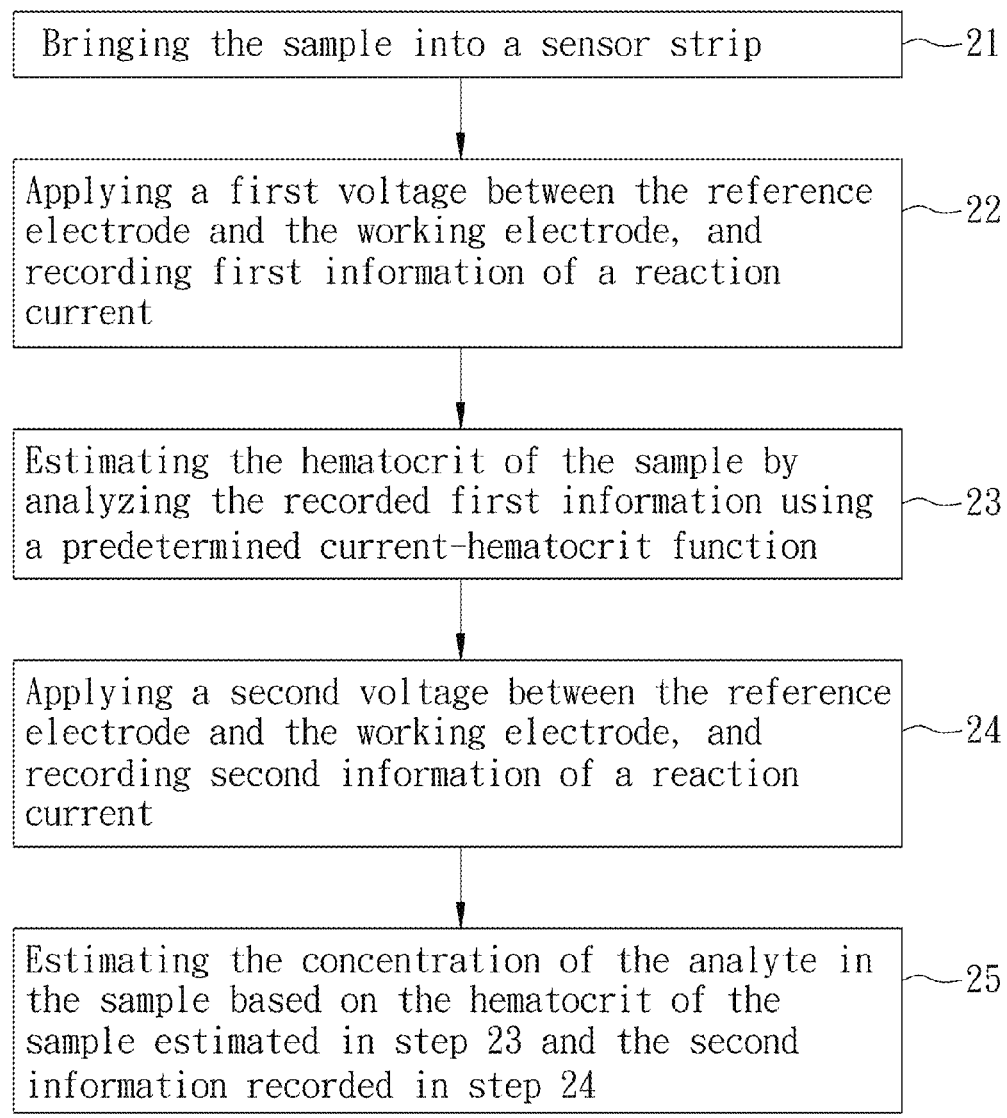
FIG. 8 is a flow chart showing steps of the preferred embodiment of the method according to the present invention.

Referring to FIGS. 4, 5, 8, the steps of a method for measurement of the sample comprises the following steps 21~25.

Step 21: Bringing the sample into contact with the sensor strip 4. The sensor strip 4 includes the reference electrode 44 coated with the reference layer 46, and the working electrode 45 coated with the working layer 47. The reference layer 46 is nonreactive to the analyte. The working layer 47 includes the mediator for enhancement of electron transfer, and the biorecognition element reactive to the analyte. In this embodiment, the sample flows from the reference electrode 44 to the working electrode 45 by capillary action.

Step 22: applying a first voltage between the reference electrode 44 and the working electrode 45 after the sample covers both of the reference electrode 44 and the working electrode 45, such that an electrical potential at the reference electrode 44 is higher than that at the working electrode 45, and recording first information of a reaction current flowing through the sample as a result of application of the first voltage within a time period of not greater than 5 seconds from beginning of application of the first voltage. That is, the overall length of the time period is included within 5 seconds counted from beginning of application of the first voltage, but the length of the time period of recording the first information is not limited. For example, the first information of the reaction current may be recorded from the $0.3^{rd}$ second to the $1.3^{rd}$ second, from the $2^{nd}$ second to the $3^{rd}$ second, from the $3^{rd}$ second to the $5^{th}$ second, or from the $0^{th}$ second to the $4^{th}$ second, etc., where the $0^{th}$ second is defined as the time point of beginning of application of the first voltage. Preferably, the first information of the reaction current is recorded within the time period of not greater than 2 seconds from beginning of application of the first voltage. More preferably, the first information of the reaction current is recorded within the time period of not greater than 1 second from beginning of application of the first voltage. The first information is associated with the reaction current and the reaction time. In this embodiment, since the reference layer 46 coated on the reference electrode 44 does not include any biorecognition element reactive to the analyte, and due to the arrangements of the reference and working electrodes 44, 45, the biorecognition element and the mediator coated on the working electrode 45 are unlikely to flow to the reference electrode 44 within a short time during application of the first voltage. The first information is thus related to hematocrit of the sample and is unrelated to the analyte in the sample. Moreover, because the reference layer 46 coated on the reference electrode 44 includes the mediator for enhancement of electron transfer, to thereby accelerate velocity of electron transfer, a higher reaction current results, and current data corresponding to hematocrit ranging from 25% to 70% is more readily identified, thus resulting in more precise estimation of hematocrit in the following steps. The first information may be obtained through the following computations: (1) a single current value or an accumulated current value based on multiple current values; (2) a value obtained by differentiation of a single or multiple current values; (3) a value obtained by accumulation or differentiation of absolute values of a single or multiple current values; (4) a logarithmic value of a single or multiple current values; and (5) a slope of a single or multiple current values.

Step 23: estimating the hematocrit of the sample by analyzing the recorded first information using a predetermined current-hematocrit function obtained by computation of known time-current and hematocrit relations pre-established in a database. The time-current and hematocrit relations may be established by repeating steps 21, 22 using samples with known hematocrit and known concentration of the analyte. The recorded first information used in this step is obtained a predetermined time period after start of application of the voltage. The obtained hematocrit in this step is considered to be not influenced by the analyte. Even though the substances of the working layer 47 may diffuse to the reference layer 46, the effect thereof can be ignored due to recording of the first information before completion of the diffusion. It should be noted that, the current-hematocrit function may be expressed using an equation, a deduction theorem, a lookup table, etc., for estimation of the hematocrit.

Step 24: applying a second voltage between the reference electrode 44 and the working electrode 45, such that an electrical potential at the reference electrode 44 is lower than that at the working electrode 45, and recording second information of a reaction current flowing through the sample as a result of application of the second voltage. The second information is associated with the reaction current and the reaction time. In this embodiment, since the working layer 47 coated on the working electrode 45 includes the biorecognition element reactive to the analyte, it is known from the Cottrell equation that the second information is related to both of the concentration of the analyte in the sample and the hematocrit of the sample. In this embodiment, amplitudes of the first and second voltages may be the same or different.

It should be noted that, due to the reference and working layers 46, 47 coated on the reference and working electrodes 44, 45 are rapidly dissolved, and directions of the reaction currents obtained during applications of the first and second voltages are different, the first and second information generated as a result of application of the first and second voltages do not interfere with and are not limited by each other. Under this condition, they can be considered as two independent reaction systems.

Step 25: estimating the concentration of the analyte in the sample based on the hematocrit of the sample estimated in step 23 and the second information recorded in step 24. In detail, the second information is first corrected using a compensation function, and the concentration of the analyte in the sample is estimated based on the corrected second information and the hematocrit of the sample estimated in step 23. In this embodiment, the second information is multiplied by a correction factor to obtain the corrected second information, and the concentration of the analyte in the sample is estimated with reference to the hematocrit estimated in step 23 and known time-current and concentration relations pre-established in the database. The time-current and concentration relations may be established by repeating steps 21, 22, 24 using samples with known hematocrit and known concentration of the analyte.

Figure 9A:
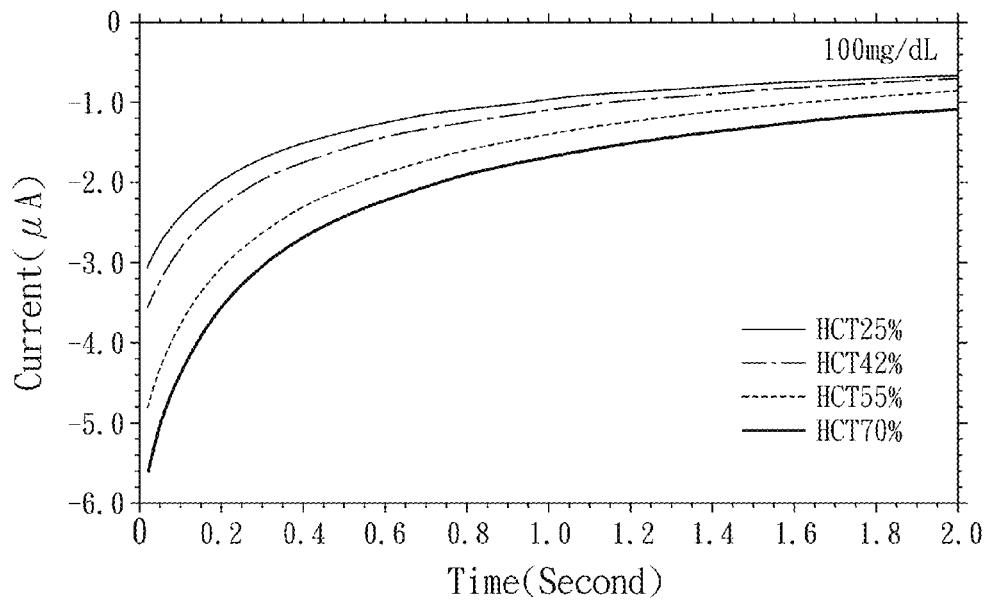
FIGS. 9(A) to 9(C) are plots showing time-current relations of samples with different hematocrits.
Figure 9B:
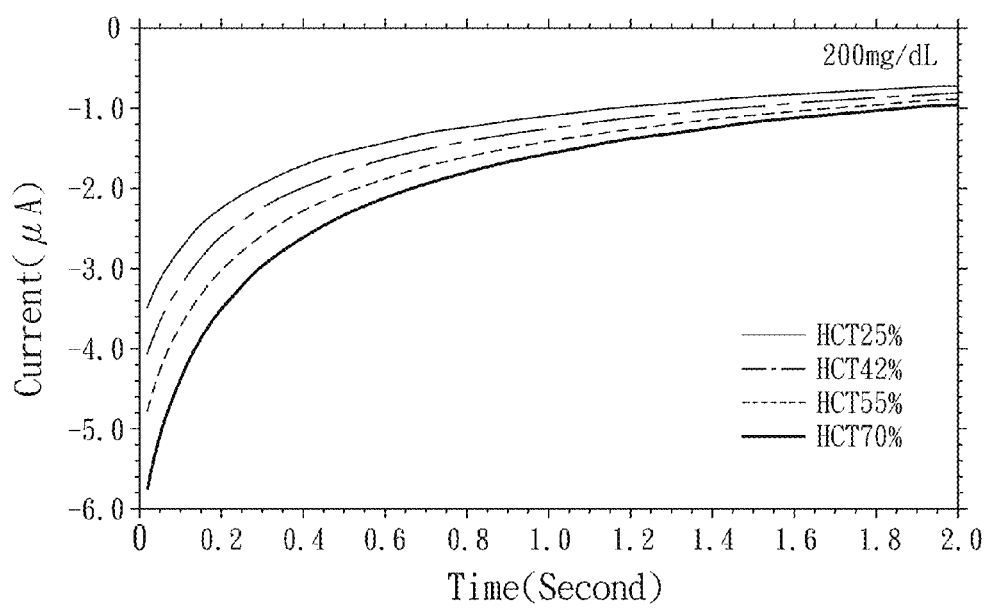
Figure 9C:
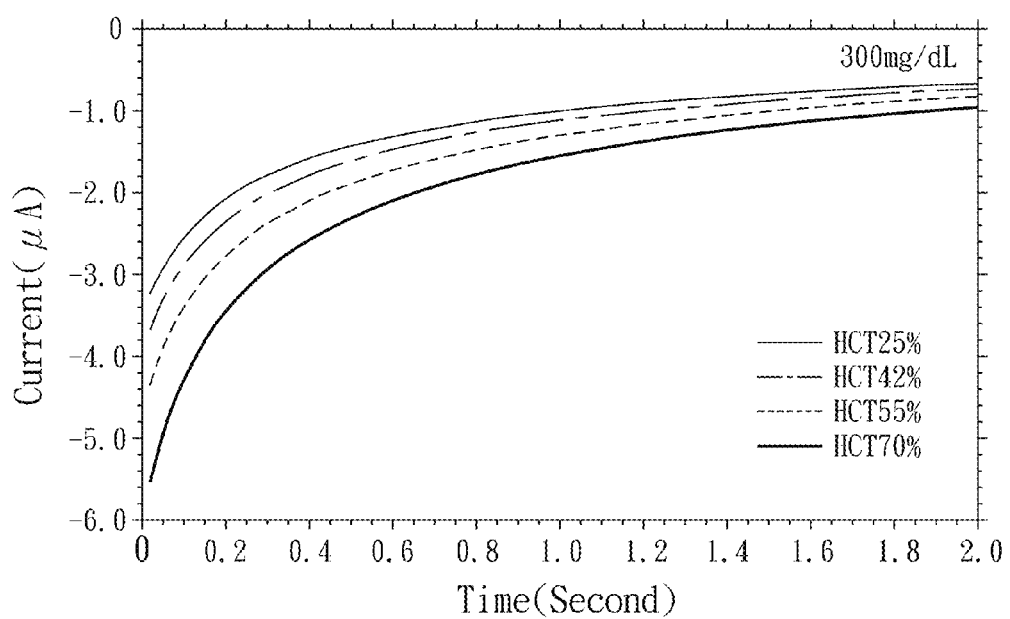
Figure 10A:
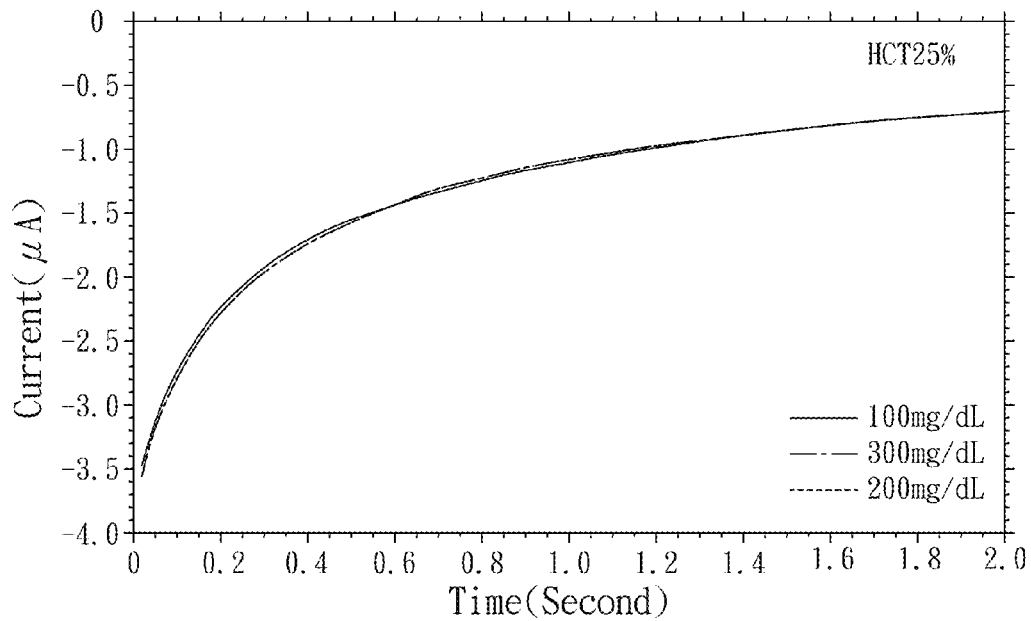
FIGS. 10(A) to 10(D) are plots showing time-current relations of samples with different concentrations of the analyte.
Figure 10B:
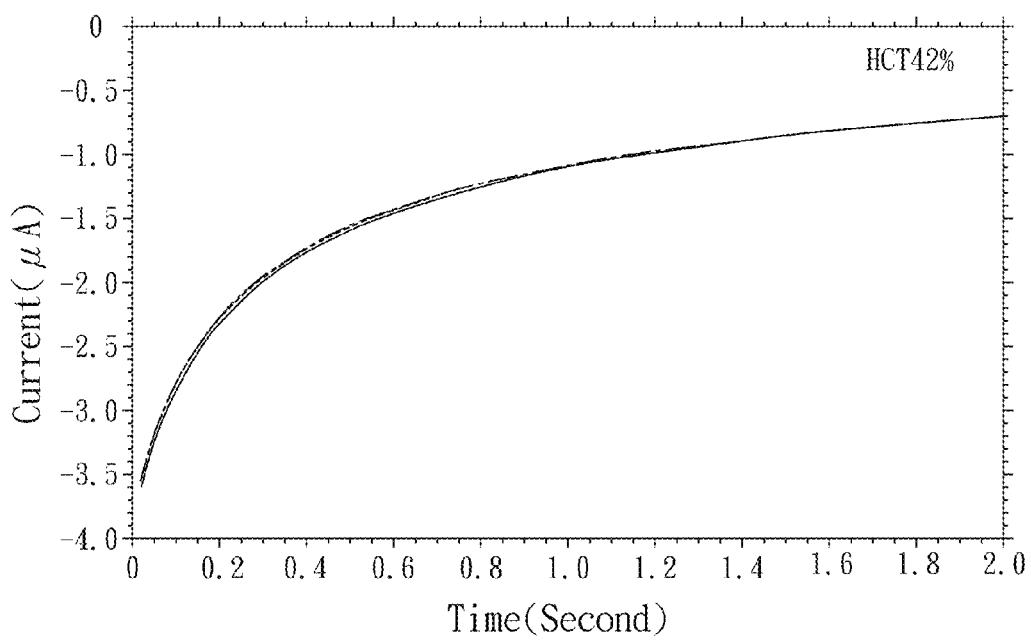
Figure 10C:
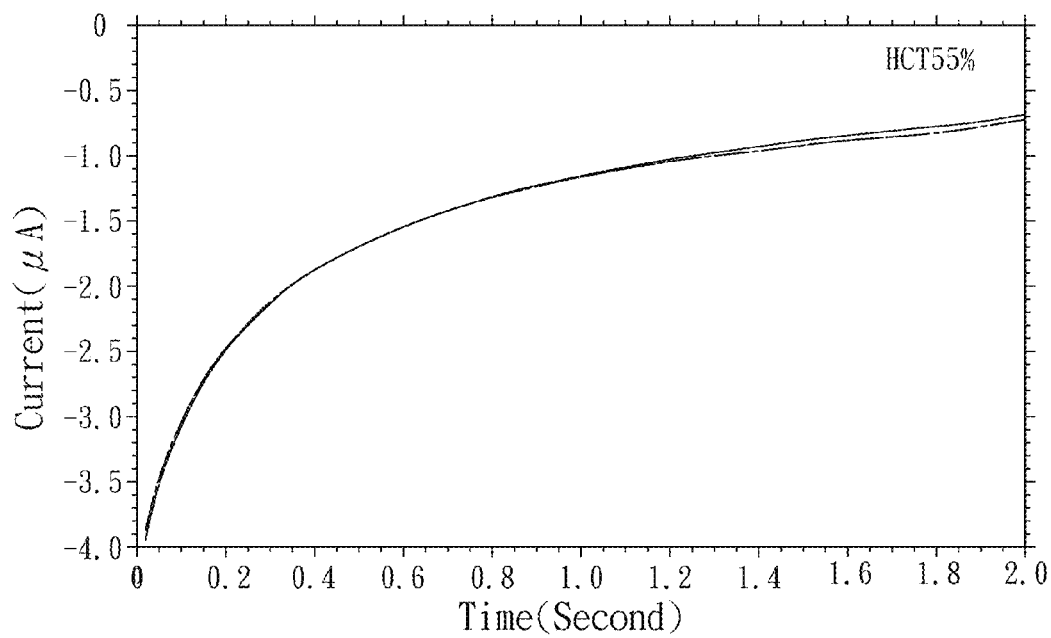
Figure 10D:
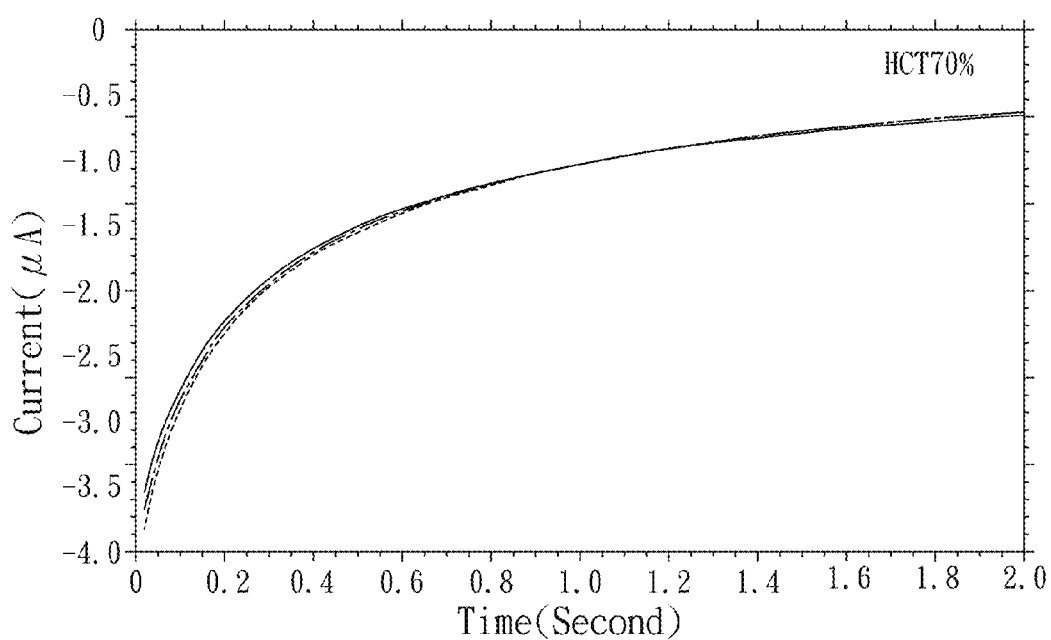

To verify the feasibility of the present invention, an experiment was performed using samples with four different hematocrits (25%, 42%, 55%, and 70%) and different concentrations (100 mg/dL, 200 mg/dL, and 300 mg/dL) of glucose as the analyte. In the process for measuring the first information, within 2 seconds from beginning of application of 0.2 VDC as the first voltage, the first information was measured and recorded. Referring to FIGS. 9(A) to 9(C), it is known that under the same concentration of the analyte, different hematocrits influence the first information. From the results shown in FIGS. 10(A) to 10(D), it is known that under the same hematocrit of the sample, different concentrations of the analyte do not influence the first information.

Because the first information and the hematocrit have a corresponding relationship, it is possible to estimate the concentration of the analyte by estimation of the hematocrit without influence by the analyte, followed by computation using the corrected second information based on the estimated hematocrit for analysis of the sample.

Figures 11A, 11B:
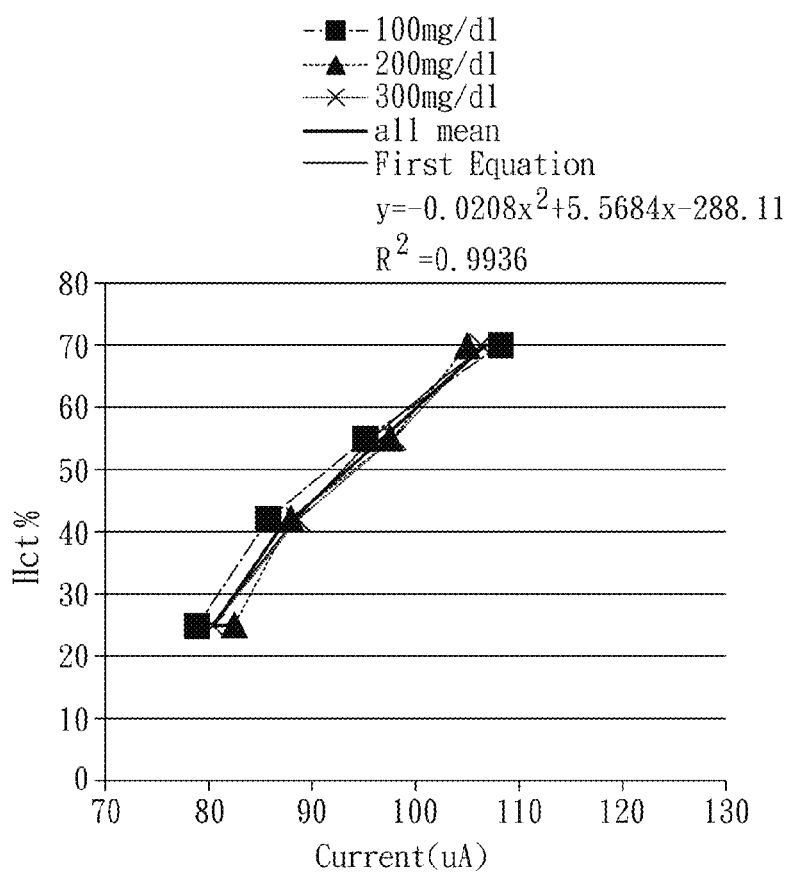
FIGS. 11(A) and 11(B) are a table showing a first database, and a plot according to the first database of an example of the present invention.

The method of this invention is illustrated using the following example. FIGS. 11(A) and 11(B) show a first database established by applying a positive first voltage between the reference electrode 44 and the working electrode 45 and measuring first reaction current values using different samples with known HCTs and known glucose concentration, and a plot according to the first database. A first equation is obtained by approximation of the mean values of the measured first reaction currents. The obtained first equation is: $y=-0.0208x^2+5.5684x-288.11$, where y is the HCT, and x is the first reaction current value.

Then, the method of this invention is applied to a sample with an unknown HCT and an unknown glucose concentration. In this example, the analyte is the glucose. According to the descriptions of steps 22 and 23, a positive first voltage is applied between the reference and working electrodes 44, 45, and a first reaction current value is recorded as 79.25983 μA, and the HCT of the sample is estimated as 22.57% by using the first reaction current value in the first equation. However, since the first database in this example only includes data of the HCT being 25% 42%, 55%, and 70%, the estimated HCT is set as 25% for facilitating the following calculation.

Figure 12C:
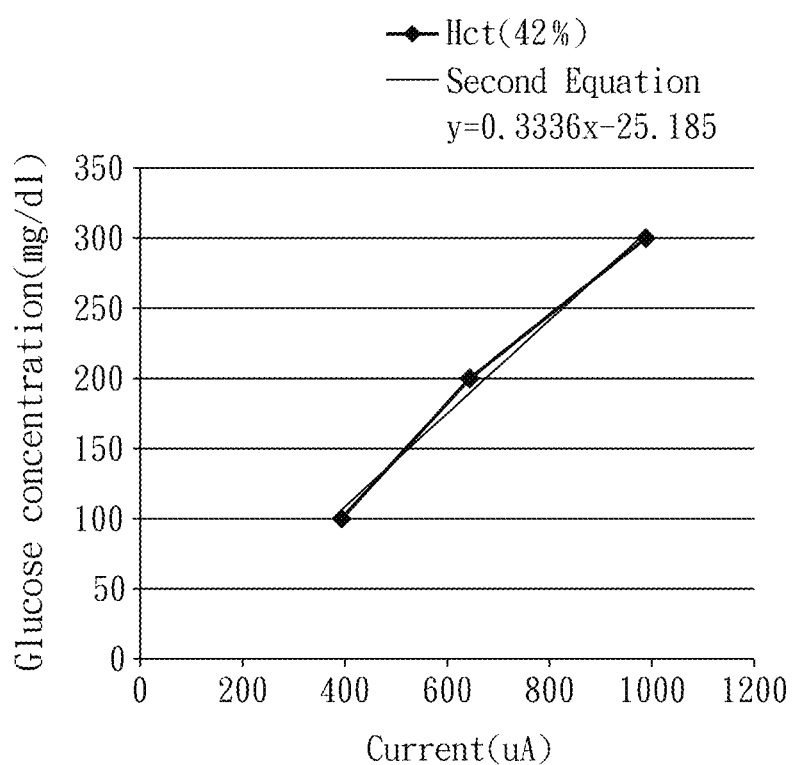

According to the descriptions of steps 24 and 25, a negative second voltage is applied between the reference and working electrodes 44, 45, and a second reaction current value is recorded as 387.83 μA. FIG. 12(A) shows a second database established by applying a negative second voltage between the reference electrode 44 and the working electrode 45 and measuring the mean values of second reaction current values using the different samples with known HCTs and known glucose concentrations. FIG. 12(B) shows a correction factor database obtained from the second database using the following equation:

$$\text{Correction Factor} = \frac{\text{The Mean } I_2 \text{ of } Hct\ 42\%}{\text{The Mean } I_2 \text{ of Each } Hct}$$

where $I_2$ is the second reaction current value. FIG. 12(C) shows a plot according to the data of the HCT being 42% in the second database. A second equation is obtained by approximation of the measured second reaction current values with the HCT being 42% in the second database. The obtained second equation is: $y=0.3336x-25.185$, where y is the glucose concentration, and x is the second reaction current value. According to the HCT estimated in step 23 and the second database, it is known that the second reaction current value (387.83) is approximate to the mean value (383.71) of second reaction current of 100 mg/dL glucose concentration. In this example, a correction factor is obtained from the second database of glucose concentration being 100 mg/dL by dividing the second reaction current of HCT 42% using the second reaction current of the estimated HCT of the sample, which is 25% in this example, and the correction factor is obtained as 1.03 (393.91/383.71≈1.03). The measured second reaction current value is then corrected by multiplication with the correction factor, and a corrected second reaction current value is obtained as 398.14 μA (387.83×1.03=399.46). Finally, the glucose concentration in the sample is estimated by using the corrected second reaction current value in the second equation in the FIG. 12(C), and is found to be about 108 mg/dL.

Figure 13A:
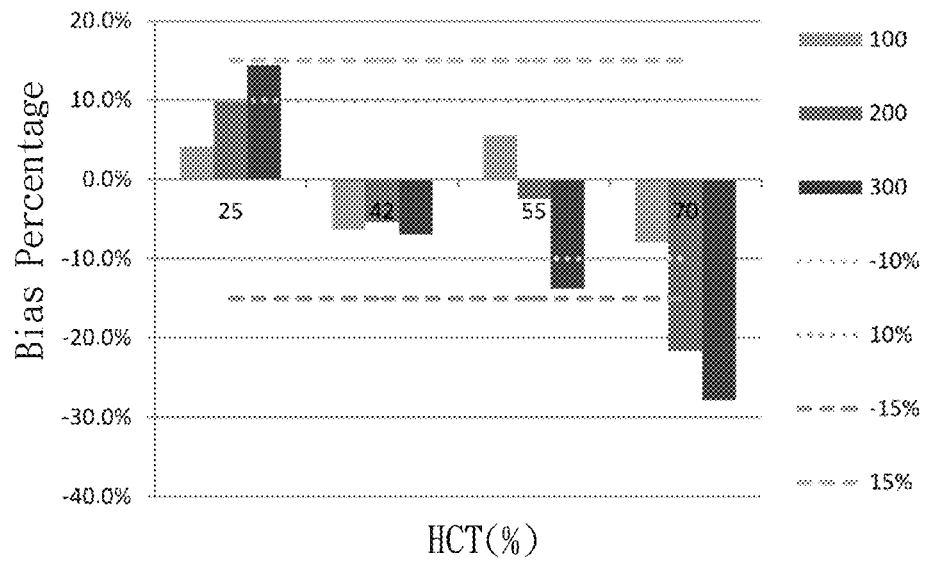
FIGS. 13(A) and 13(B) are plots showing improved effect of the method according to the present invention.
Figure 13B:
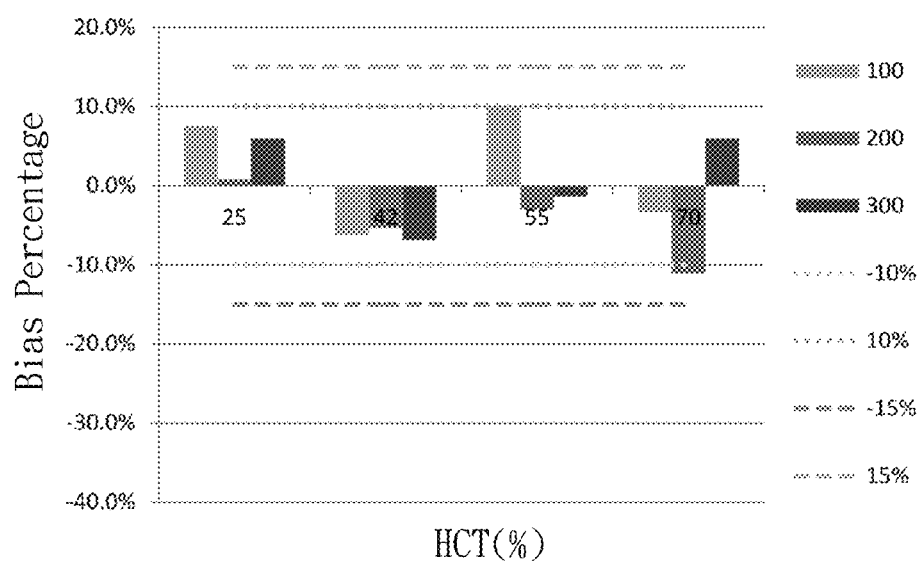

In order to verify improvement on estimation accuracy of the glucose concentration, the method of this invention is applied to various samples having different known HCTs and known glucose concentrations to obtain bias percentages of the estimated glucose concentration relative to the actual glucose concentration by using the measured second reaction current values in the second equation, as shown in FIG. 13(A), and using the corrected second reaction current values in the second equation, as shown in FIG. 13(B). From FIGS. 13(A) and (B), it is evident that the bias percentages of the estimated glucose concentrations are improved when the method of this invention is used. The improvements are more evident for low HCT (25%) and high HCT (70%), where the bias percentages of the glucose concentrations are reduced from about ±15%~±20% to about ±10%.

To sum up, by using the reference layer 46 which is non-reactive to the analyte, the first information is only related to the hematocrit of the sample, such that the estimated hematocrit is not related to the analyte. Compared to the conventional method for analysis of blood, the hematocrit and the concentration of the analyte obtained by the present invention can achieve higher precision, and can serve as effective reference data.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for estimation of concentration of an analyte in a sample, comprising:
   a) bringing the sample into contact with a sensor strip, the sensor strip including a reference electrode coated with a reference layer, and a working electrode coated with a working layer, and being configured such that the sample flows from the reference electrode to the working electrode, the reference layer being nonreactive to the analyte, the working layer including a mediator for enhancement of electron transfer, and a biorecognition element reactive to the analyte;
   b) applying a first voltage between the reference electrode and the working electrode, such that an electrical potential at the reference electrode is higher than that at the working electrode, and recording first information of a reaction current flowing through the sample as a result of application of the first voltage within a time period of not greater than 5 seconds from beginning of application of the first voltage, wherein the first information is related to hematocrit of the sample and is unrelated to the analyte in the sample;
   c) estimating the hematocrit of the sample by analyzing the recorded first information using a predetermined current-hematocrit function;
   d) applying a second voltage between the reference electrode and the working electrode, such that an electrical potential at the reference electrode is lower than that at the working electrode, and recording second information of a reaction current flowing through the sample as a result of application of the second voltage, wherein the second information is related to the concentration of the analyte in the sample; and
   e) estimating the concentration of the analyte in the sample based on the hematocrit of the sample estimated in step c) and the second information recorded in step d).

2. The method as claimed in claim 1, wherein the reference layer includes a mediator for enhancement of electron transfer.

3. The method as claimed in claim 2, wherein the reference layer further includes an anionic surfactant.

4. The method as claimed in claim 1, wherein the sample is blood.

5. The method as claimed in claim 1, wherein the biorecognition element is an enzyme.

6. The method as claimed in claim 1, wherein step e) includes:
   e1) correcting the second information using a compensation function; and
   e2) estimating the concentration of the analyte in the sample based on the corrected second information and the hematocrit of the sample estimated in step c).

7. The method as claimed in claim 6, wherein, in sub-step e1), the second information is multiplied by a correction factor to obtain the corrected second information.

8. The method as claimed in claim 1, wherein, in step e), the concentration of the analyte in the sample is estimated with reference to the hematocrit estimated in step c) and known time-current and concentration relations pre-established in a database.

9. The method as claimed in claim 1, wherein, in step b), the first information is recorded within the time period in which effect of diffusion of substances of the working layer to the reference layer can be ignored such that the first information is unrelated to the analyte in the sample.

10. The method as claimed in claim 1, wherein the sensor strip further includes a strip body formed with a groove for receiving the sample;
    wherein the reference electrode is adjacent to the groove; and
    the working electrode is spaced apart from the reference electrode, and is adjacent to said groove.

11. The method as claimed in claim 10, wherein the groove has a sample inlet for introducing the sample, and the sample inlet is closer to the reference electrode than the working electrode.

12. The method as claimed in claim 11, the reference layer includes a mediator for enhancement of electron transfer, and a hydrophilic chemical substance, and the working layer further includes a hydrophilic chemical substance.

13. The method as claimed in claim 12, wherein the reference layer does not include any enzyme reactive to the analyte.

14. The method as claimed in claim 11, wherein the reference electrode and the working electrode are disposed side by side on a same plane.

15. The method as claimed in claim 5, wherein the sensor strip does not include any electrode coated with a layer including an enzyme reactive to the analyte other than the working electrode.

16. The method as claimed in claim 9, wherein the sensor strip further includes a strip body formed with a groove for receiving the sample;

wherein the reference electrode is adjacent to the groove;

the working electrode is spaced apart from the reference electrode, and is adjacent to said groove; and the sample inlet is closer to the reference electrode than the working electrode.

* * * * *